United States Patent [19]

Patel et al.

[11] Patent Number: 5,165,943
[45] Date of Patent: Nov. 24, 1992

[54] COOLING AGENT/CYCLODEXTRIN COMPLEX FOR IMPROVED FLAVOR RELEASE

[75] Inventors: Mansukh H. Patel, Downers Grove; Steven A. Hvizdos, Woodridge, both of Ill.

[73] Assignee: Wm. Wrigley Jr. Company, Chicago, Ill.

[21] Appl. No.: 718,328

[22] Filed: Jun. 21, 1991

[51] Int. Cl.⁵ .................... A23L 1/236; A23L 1/09
[52] U.S. Cl. ........................... 426/3; 426/658; 426/532; 426/537
[58] Field of Search ...................... 426/3–6, 426/532, 537, 658

[56] References Cited

U.S. PATENT DOCUMENTS

| | | | |
|---|---|---|---|
| 4,267,166 | 5/1981 | Yajima | 426/3 |
| 4,459,425 | 7/1984 | Amano et al. | 426/101 |
| 4,751,095 | 6/1988 | Karl et al. | 426/654 |
| 4,789,559 | 12/1988 | Hirao et al. | 426/3 |

*Primary Examiner*—Jeanette Hunter
*Attorney, Agent, or Firm*—Willian Brinks Olds Hofer Gilson & Lione

[57] ABSTRACT

The present invention is directed to inclusion complexes formed between 3-1-menthoxypropane-1,2-diol and a cyclodextrin selected from the group consisting of alpha-cyclodextrin, beta-cyclodextrin, gamma-cyclodextrin and mixtures thereof. The present invention is further directed to chewing gums containing such inclusion complexes.

23 Claims, No Drawings

COOLING AGENT/CYCLODEXTRIN COMPLEX FOR IMPROVED FLAVOR RELEASE

BACKGROUND OF THE INVENTION

Various compounds having cooling activity are known which are perceived as cold or cool when contacted with the human body and, in particular, with the mucous membranes of the mouth, nose and throat. An example of such a compound is 3-1-menthoxypropane-1,2-diol, which is the subject of U.S. Pat. No. 4,459,425.

The present invention is directed to novel inclusion complexes formed between 3-1-menthoxypropane-1,2-diol and a cyclodextrin. This inclusion complex can be used in chewing gum to improve the "cool" taste perceived upon chewing the gum without substantially effecting the gum's texture.

SUMMARY OF THE INVENTION

The present invention is directed to novel chewing gums containing novel inclusion complexes formed between 3-1-menthoxypropane-1,2-diol and a cyclodextrin.

In one feature of the present invention, a method of making an inclusion complex formed between 3-1-menthoxypropane-1,2-diol and a cyclodextrin is provided. According to this method, 3-1-menthoxypropane-1,2-diol and a cyclodextrin selected form the group consisting of alpha-cyclodextrin, beta-cyclodextrin, gamma-cyclodextrin, and mixtures thereof, are mixed in an aqueous medium to form an inclusion complex between the cyclodextrin and 3-1-menthoxypropane-1,2-diol. Preferably, the inclusion complex is made by mixing greater than about a 1:1 molar ratio of 3-1-menthoxypropane-1,2-diol to beta-cyclodextrin.

In another feature of the present invention, an inclusion complex is provided which is formed between 3-1-menthoxypropane-1,2-diol and a cyclodextrin selected from the group consisting of alpha-cyclodextrin, beta-cyclodextrin, gamma-cyclodextrin and mixtures thereof. Preferably, an inclusion complex is provided which is formed between 3-1-menthoxypropane-1,2-diol and beta-cyclodextrin.

In another aspect of the present invention, a method of making a chewing gum is provided. According to this method, an inclusion complex formed between 3-1-menthoxypropane-1,2-diol and a cyclodextrin selected from the group consisting of alpha-cyclodextrin, betacyclodextrin, gamma-cyclodextrin, and mixtures thereof, is mixed with chewing gum ingredients. Preferably, an inclusion complex formed between 3-1-menthoxypropane-1,2-diol and beta-cyclodextrin is mixed with chewing gum ingredients in such amounts so that the inclusion complex comprises from about 0.1% to about 7% by weight of the chewing gum. Additionally, an amount of free 3-1-menthoxypropane-1,2-diol may be mixed with the chewing gum ingredients such that the free 3-1-menthoxypropane-1,2-diol comprises from about 0.01% to about 0.5% by weight of the chewing gum.

In another feature of the present invention, a chewing gum is provided comprising an inclusion complex formed between 3-1-menthoxypropane-1,2-diol and a cyclodextrin selected from the group consisting of alpha-cyclodextrin, beta-cyclodextrin, gamma-cyclodextrin and mixtures thereof. Preferably, the chewing gum will comprise about 0.1 to about 7% by weight of an inclusion complex formed between beta-cyclodextrin and 3-1-menthoxypropane-1,2-diol. Additionally, the chewing gum may further comprise from about 0.0% to about 0.5% by weight of free 3-1-menthoxypropane-1,2-diol.

DETAILED DESCRIPTION OF PREFERRED EMBODIMENTS

Cooling agents have a physiological cooling effect. Cooling agents can be used in foodstuffs, drinks, dentrifices, gargles, cosmetics, tobacco products, abrasives, lotions, etc. Examples of some cooling agents include menthol, 3-substituted-P-menthanes, N-substituted-P-menthane-3-carboxamides and 3-1-menthoxypropane-1,2-diol. The present invention is directed in particular to 3-1-menthoxypropane-1,2-diol. When 3-1-menthoxypropane-1,2-diol is present in chewing gum, a "coolness" is perceived upon chewing the gum. A relatively high level of the 3-1-menthoxypropane-1,2-diol is required to impart the desired coolness sensation in chewing gum. However, where high levels of 3-1-menthoxypropane-1,2-diol are used in the chewing gum, the gum base tends to undergo undesirable base softening. To combat this softening problem, a modified gum base must be used where relatively high levels of 3-1-menthoxypropane-1,2-diol is added. The need for a modified gum base is both inconvenient and expensive because it may require the stocking of an additional gum base. Ideally, all of a manufacturer's gum products, regardless of other ingredients, would use the same base. It has unexpectedly been discovered that the gum base softening effect caused by the addition of 3-1-menthoxypropane-1,2-diol is minimized, and thus the need for a modified gum base, by encapsulating the 3-1-menthoxypropane-1,2-diol in cyclodextrin prior to its addition to the chewing gum.

Pursuant to the present invention, 3-1-menthoxypropane-1,2-diol is encapsulated by an inclusion complex formed between the 3-1-menthoxypropane-1,2-diol and a cyclodextrin. This inclusion complex is a clathrate wherein the 3-1-menthoxypropane-1,2-diol is included in the cyclodextrin at the molecular level. When the gum is chewed, the inclusion complex dissolves gradually releasing the 3-1-menthoxypropane-1,2-diol. In addition to minimizing the aforesaid base softening effect, the inclusion complex formed between 3-1-menthoxypropane-1,2-diol and cyclodextrin provides a peak coolness perception with the initial flavor impact without an associated diminution of the cool sensation during the later stages of the chew.

Cyclodextrins contemplated for use in the present invention have circular structures and are capable of forming inclusion complexes with 3-1-menthoxypropane-1,2-diol. Cyclodextrins with which the present invention is concerned include alpha-cyclodextrin, betacyclodextrin, gamma-cyclodextrin and mixtures thereof. Alpha-cyclodextrin is a ring-structured compound comprising six glucopyranose units; beta-cyclodextrin is a ring-structured compound comprising seven glucopyranose units; and gamma-cyclodextrin is a ring-structured compound having eight glucopyranose units. Further details on cyclodextrin can be gleaned from U.S. Pat. No. 4,751,095, incorporated by reference herein. Cyclodextrins are commercially available and may be utilized in the present invention without modification. One source of beta-cyclodextrin contemplated for use in the present invention is sold as Item No. 11968 by Roquette Corporation, Gurnee, IL.

In one embodiment of the present invention, a method of making an inclusion complex of 3-1-menthoxypropane-1,2-diol with cyclodextrin is provided. The cyclodextrin is selected from the group consisting of alpha-cyclodextrin, beta-cyclodextrin, gammacyclodextrin and mixtures thereof. Preferably, the cyclodextrin will be beta-cyclodextrin. The inclusion complex is formed by dissolving the cyclodextrin in a medium suitable for the formation of the inclusion complex. Suitable mediums include aqueous liquids in which the cyclodextrin is soluble and in which the 3-1-menthoxypropane-1,2-diol is capable of being dispersed. A preferred medium is water. However, an aqueous liquid comprising primarily water with small amounts of alcohol are suitable as well. For example, aqueous solutions of methanol, ethanol or isopropanol in which the cyclodextrin is soluble are suitable for use in the present invention.

The cyclodextrin is dissolved in the aqueous medium at a level below its solubility limit. To this solution the 3-1-menthoxypropane-1,2-diol is slowly added while simultaneously stirring the solution to disperse the water-insoluble 3-1-menthoxypropane-1,2-diol. As the 3-1-menthoxypropane-1,2-diol/cyclodextrin complex is formed, the insoluble product drops out of solution. As the cyclodextrin is used up, more can be added to maintain the optimum complexing rate. Preferably, greater than a 1:1 molar ratio of 3-1-menthoxypropane-1,2-diol to cyclodextrin should be maintained. A continuous complexing process is established by maintaining a 2:1 molar ratio of 3-1-menthoxypropane-1,2-diol to cyclodextrin. The final inclusion complex product is separated from the medium by any method of separation known by those skilled in the art. Preferably, the inclusion complex is separated pursuant to mechanical means such as filtration, decantion or centrifugation.

After separation of the inclusion complex formed between 3-1-menthoxypropane-1,2-diol and cyclodextrin, it may be dried according to any method of drying known by those skilled in the art, as for example, air drying, spray-drying, freeze-drying, heat and/or low pressure drying. However, air drying is preferred.

In another embodiment of the present invention, the inclusion complex formed between 3-1-menthoxypropane-1,2-diol and cyclodextrin is combined with chewing gum ingredients to form a chewing gum. Preferably, the inclusion complex will be made prior to mixing with the chewing gum ingredients. The inclusion complex may be mixed with the chewing gum ingredients at any time during the manufacturing process. Preferably, the inclusion complex will be mixed in such amounts so that it comprises from about 0.1% to about 7% by weight of the chewing gum. More preferably, the inclusion complex will comprise from about 0.5% to about 3% by weight of the chewing gum. Most preferably, the inclusion complex will comprise from about 1% to about 2% by weight of the chewing gum.

Optionally, free 3-1-menthoxypropane-1,2-diol may also be mixed with the chewing gum ingredients and inclusion complex. The free 3-1-menthoxypropane-1,2-diol may be mixed at any time with the chewing gum ingredients, but preferably it is added late in the mix. Preferably, free 3-1-menthoxypropane-1,2-diol will be mixed in such amounts so that it comprises from about 0.01% to about 0.5% by weight of the chewing gum. More preferably, the free 3-1-menthoxypropane-1,2-diol will comprise from about 0.05% to about 0.2% by weight of the chewing gum. Most preferably, the free 3-1-menthoxypropane-1,2-diol will comprise from about 0.08% to about 0.12% by weight of the chewing gum.

The inclusion complex of cyclodextrin and 3-1-menthoxypropane-1,2-diol, as well as free 3-1-menthoxypropane-1,2-diol, are contemplated for use in any chewing gum known by those skilled in the art. Preferably, however, the inclusion complex is used in a mint-flavored chewing gum such as that disclosed in the example herein.

In general, a chewing gum composition comprises a water-soluble bulk portion, a water insoluble chewable gum base portion, and typically water insoluble flavor. The water-soluble bulk portion dissipates with a portion of the flavor over a period of time during chewing. The insoluble gum-base is retained in the mouth throughout the chew.

The insoluble gum base generally comprises elastomers, resins, fats and oils, waxes, softeners and inorganic fillers. Elastomers are present in an amount from about 10% to about 30% by weight of the chewing gum base, and may include polyisobutylene, isobutyleneisoprene copolymer, styrene-butadiene rubber, as well as natural latexes such as chicle. Resins are present in an amount from about 15% to about 30% by weight of the chewing gum base, and may include polyvinyl acetate and terpene resins. Fats and oils may also be included in the gum base in an amount from about 15% to about 40% by weight of the gum base, and include tallow, hydrogenated and partially hydrogenated vegetable oils and cocoa butter. Waxes are present in an amount from about 0.1% to about 15% by weight of the gum base, and may include paraffin wax, microcrystalline wax and natural waxes such as beeswax and carnauba.

The gum base typically includes a filler component. The filler component may be calcium carbonate, magnesium carbonate, talc, dicalcium phosphate and the like, as well as mixtures thereof. The filler may constitute between about 5 to about 60 weight percent of the gum base. Preferably, the filler comprises about 5 to about 50 weight percent of the chewing gum base.

The gum base typically also contains softeners and emulsifiers. Softeners include glycerol monostearate and glycerol triacetate. Emulsifiers may comprise from about 1% to about 10% by weight of the gum base, and include lecithin, fatty acid monoglycerides, triglycerides and the like, as well as mixtures thereof. Further, gum bases may also contain optional ingredients such as anti-oxidants, colors and emulsifiers.

The insoluble gum base constitutes between about 5 to about 95 weight percent of the gum. Preferably, the insoluble gum base comprises about 10 to about 50 weight percent of the gum, and more preferably, about 20 to about 30 weight percent.

The water-soluble portion of chewing gum may comprise softeners, sweeteners, flavors and combinations thereof. The softeners are added to the chewing gum in order to optimize the chewability and mouth-feel of the gum. Softeners, also known in the art as plasticizers or plasticizing agents, generally constitute between about 0.1% to about 15% by weight of the chewing gum. Softeners contemplated by the present invention include glycerin, lecithin and combinations thereof. Further, aqueous sweetener solutions such as those containing sorbitol, hydrogenated starch hydrolysates, corn syrup and combinations thereof may be used as softeners and binding agents in gum.

Sweeteners contemplated for use in chewing gum include both sugar and sugarless components. Sugar sweeteners generally include saccharide-containing components, commonly known in the chewing gum art which comprise but are not limited to sucrose, dextrose, maltose, dextrin, dried invert sugar, fructose, levulose, galactose, corn syrup solids, and the like, alone or in any combination. Sugarless sweeteners generally include components with sweetening characteristics but are devoid of the commonly known sugars and are comprised but not limited to sugar alcohols such as sorbitol, mannitol, xylitol, hydrogenated starch hydrolysates, maltitol, and the like, alone or in any combination. Also contemplated for direct addition to the gum are relatively faster-releasing, high intensity sweeteners, such as aspartame, sucrose, acesulfame-K, alitame and saccharin.

Those skilled in the art will recognize that any combination of sugar and/or sugarless sweeteners may be employed in the chewing gum. Further, those skilled in the art will recognize a sweetener may be present in a chewing gum in whole or in part as a water-soluble bulking agent. In addition, the softener can be combined with a sweetener such as an aqueous sweetener solution.

Chewing gum also contains flavor. Flavor is present in chewing gum from about 0.1% to about 10% by weight, and preferably from about 0.5% to about 3% by weight of the gum. Flavors contemplated by the present invention include any liquid flavoring which is of food acceptable quality. Such flavors may consist of essential oils, synthetic flavors, and mixtures thereof, including but not limited to oils derived from plants and fruits such as citrus oils, fruit essences, peppermint oil, spearmint oil, clove oil, oil of wintergreen, anise, and the like. Artificial flavoring components are also contemplated by the present invention. Those skilled in the art will recognize that the natural and artificial flavor can be combined in any manner.

Ingredients such as colors, emulsifiers, and pharmaceutical agents may be added to the chewing gum.

In general, chewing gum is manufactured by sequentially adding the various chewing gum ingredients to any mixer known in the art. After the ingredients have been thoroughly mixed, the gum mass is discharged from the mixer and shaped into the desired forms, such as by rolling it into sheets and cutting it into sticks, extruding into chunks, or casting into pellets. Generally, the ingredients are mixed by first melting the gum base and adding it to the running mixer. The base may also be melted in the mixer itself. Color may also be added at this time. A softener such as glycerin may then be added next along with syrup and a portion of the bulking agent. Further portions of the bulking agent may then be added to the mixer. It should be understood that the inclusion complex of the present invention may be added at any time during the gum manufacturing process.

The entire mixing procedure typically takes from about 5 to about 15 minutes, but longer mixing times may sometimes be required.

Of course, it should be understood that a wide range of changes and modifications can be made to the preferred embodiments described above. This invention is believed applicable to confectioneries other than chewing gum. It is therefore intended that the foregoing detailed description be regarded as illustrative rather than limiting, and that it be understood that it is the claims appended hereto, including all equivalents, which are intended to define the scope of this invention.

EXAMPLE

A sample of an inclusion complex was formed between 3-1-menthoxypropane-1,2-diol and betacyclodextrin (Roquette Corp., Gurnee, IL (Item No. 11968) having 16.8% loading (i.e. 16.8% by weight of 3-1-menthoxypropane-1,2-diol). Two samples of chewing gum were prepared by blending the below-indicated formulations. In chewing gum "A", the 3-1-menthoxypropane-1,2-diol was added to the gum in its free form. In chewing gum "B", the 3-1-menthoxypropane-1,2-diol was added pursuant to the abovedescribed inclusion complex.

| Ingredients | Chewing Gum A (% by Weight) | Chewing Gum B (% by Weight) |
| --- | --- | --- |
| Base | 24.93 | 24.93 |
| Sorbitol | 45.26 | 44.22 |
| Mannitol | 14.00 | 14.00 |
| Glycerin | 13.00 | 13.00 |
| Peppermint flavor | 1.70 | 1.70 |
| Lecithin | 0.50 | 0.50 |
| Aspartame | 0.40 | 0.40 |
| 3-1-menthoxypropane-1,2-diol | 0.21 | — |
| 3-1-menthoxypropane-1,2-diol/beta-cyclodextrin complex | | 1.25 |
| | 100.00 | 100.00 |

A formal sensory panel evaluated and compared chewing gums A and B. In particular, six pieces each of the two samples were coded with random three digit numbers and one piece of each formula was given to each of six expert panelists. The pieces were chewed in random order for fifteen minutes and the panelists wrote comments on each sample. After chewing both pieces, the samples were given common codes (to allow discussion among the panelists) but were not otherwise identified.

The panel results found that chewing gum B had a higher "coolness" and flavor impact. The flavor and coolness intensity of the two chewing gums after five minutes of chewing were considered the same. The texture of chewing gum B was desirably firmer than gum A.

We claim:

1. A method for making an inclusion complex formed between 3-1-menthoxypropane-1,2-diol; and cyclodextrin comprising:
   providing 3-1-menthoxypropane-1,2-diol;
   providing a cyclodextrin selected from the group consisting of:
   (a) alpha-cyclodextrin;
   (b) beta-cyclodextrin;
   (c) gamma-cyclodextrin; and
   (d) mixtures thereof;
   providing a medium in which the cyclodextrin is soluble and the 3-1-menthoxypropane-1,2-diol is capable of being dispersed; and
   mixing greater than about a 1:1 molar ratio of the 3-1-menthoxypropane-1,2-diol to cyclodextrin in the medium to form an inclusion complex.

2. The method of claim 1 wherein the molar ratio of 3-1-menthoxypropane-1,2-diol to cyclodextrin is greater than about 1:1.

3. The method of claim 1 wherein the cyclodextrin comprises beta-cyclodextrin.

4. A method of making an inclusion complex formed between 3-1-menthoxypropane-1,2-diol cyclodextrin comprising:
providing 3-1-methoxypropane-1,2-diol;
providing a cyclodextrin selected from the group consisting of:
(a) alpha-cyclodextrin;
(b) beta-cyclodextrin;
(c) gamma-cyclodextrin; and
(d) mixtures thereof;
providing a medium in which the cyclodextrin is soluble and the 3-1-menthoxypropane-1,2-diol is capable of being dispersed; and
mixing greater than about a 1:1 molar ratio of 3-1-menthoxypropane-1,2-diol to cyclodextrin in the medium to form an inclusion complex.

5. The method of claim 4 wherein the cyclodextrin comprises beta-cyclodextrin.

6. A composition comprising an inclusion complex formed between 3-1-menthoxypropane-1,2-diol and a cyclodextrin selected from the group consisting of:
(a) alpha-cyclodextrin;
(b) beta-cyclodextrin;
(c) gamma-cyclodextrin; and
(d) mixtures thereof.

7. The composition of claim 6 wherein the cyclodextrin comprises beta-cyclodextrin.

8. A method of making a chewing gum comprising:
providing an inclusion complex formed between 3-1-menthoxypropane-1,2-diol and cyclodextrin wherein the cyclodextrin is selected from the group consisting of:
(a) alpha-cyclodextrin;
(b) beta-cyclodextrin;
(c) gamma-cyclodextrin; and
(d) mixtures thereof;
providing chewing gum ingredients; and
mixing the chewing gum ingredients and the inclusion complex.

9. The method of claim 8 wherein the inclusion complex comprises from about 0.1% to about 7% by weight of the chewing gum.

10. The method of claim 8 wherein the cyclodextrin comprises beta-cyclodextrin.

11. The method of claim 8 wherein the inclusion complex comprises from about 0.5% to about 3% by weight of the chewing gum.

12. The method of claim 8 wherein the inclusion complex comprises from about 1% to about 2% by weight of the chewing gum.

13. The method of claim 8 wherein an amount of free 3-1-menthoxypropane-1,2-diol is mixed with the chewing gum ingredients and inclusion complex such that the free 3-1-menthoxypropane-1,2-diol comprises from about 0.01% to about 0.5% by weight of the chewing gum.

14. The method of claim 13 wherein the free 3-1-menthoxypropane-1,2-diol comprises from about 0.05% to about 0.2% by weight of the chewing gum.

15. The method of claim 13 wherein the free 3-1-menthoxypropane-1,2-diol comprises from about 0.08% to about 0.12% by weight of the chewing gum.

16. A chewing gum comprising an inclusion complex formed between 3-1-menthoxypropane-1,2-diol and a cyclodextrin selected from the group consisting of:
(a) alpha-cyclodextrin;
(b) beta-cyclodextrin;
(c) gamma-cyclodextrin; and
(d) mixtures thereof.

17. The chewing gum of claim 16 wherein the cyclodextrin comprises beta-cyclodextrin.

18. The chewing gum of claim 16 wherein the inclusion complex comprises from about 0.1% to about 7% by weight of the chewing gum.

19. The chewing gum of claim 16 wherein the inclusion complex comprises from about 0.5% to about 3% by weight of the chewing gum.

20. The chewing gum of claim 19 wherein the inclusion complex comprises from about 1% to about 2% by weight of the chewing gum.

21. The chewing gum of claim 18 wherein the chewing gum further comprises from about 0.01% to about 0.5% by weight free 3-1-menthoxypropane-1,2-diol.

22. The chewing gum of claim 16 wherein the chewing gum further comprises from about 0.05% to about 0.2% by weight free 3-1-menthoxypropane-1,2-diol.

23. The chewing gum of claim 16 wherein the chewing gum further comprises from about 0.08% to about 0.12% by weight free 3-1-menthoxypropane-1,2-diol.

* * * * *

UNITED STATES PATENT AND TRADEMARK OFFICE
CERTIFICATE OF CORRECTION

PATENT NO. : 5,165,943
DATED : November 24, 1992
INVENTOR(S) : Mansukh M. Patel et al.

Page 1 of 2

It is certified that error appears in the above-indentified patent and that said Letters Patent is hereby corrected as shown below:

On title page, item [75]

Under the heading "Inventors:", after "Mansukh" please delete "H." and substitute therefor --M.--.

Column 1, line 51, please delete "betacyclodextrin" and substitute therefor --beta-cyclodextrin--.

Column 2, line 4, please delete "0.0%" and substitute therefor --0.01%--.

Column 2, line 58, please delete "betacyclodextrin" and substitute therefor --beta-cyclodextrin--.

Column 3, lines 7-8, please delete "gammacyclodextrin" and substitute therefor --gamma-cyclodextrin--.

Column 4, lines 24-25, please delete "isobutyleneisoprene" and substitute therefor --isobutylene-isoprene--.

Column 6, line 8, after "11968)" please insert --)--.

Column 6, line 15, please delete "abovedescribed" and substitute therefor --above-described--.

UNITED STATES PATENT AND TRADEMARK OFFICE
CERTIFICATE OF CORRECTION

PATENT NO. : 5,165,943

DATED : November 24, 1992

INVENTOR(S) : Mansukh M. Patel et al.

It is certified that error appears in the above-indentified patent and that said Letters Patent is hereby corrected as shown below:

Column 7,

Claim 4, line 2, before "cyclodextrin" please insert --and--.

Signed and Sealed this

Fifth Day of July, 1994

Attest:

BRUCE LEHMAN

Attesting Officer    Commissioner of Patents and Trademarks